United States Patent
Lau et al.

[11] Patent Number: 5,342,943
[45] Date of Patent: Aug. 30, 1994

[54] PREPARATION OF 1H PYRAZOLO [3,2-C]-S-TRIAZOLE COMPOUNDS

[75] Inventors: Philip T. S. Lau; Ping-Wah Tang, both of Rochester, N.Y.

[73] Assignee: Eastman Kodak Company, Rochester, N.Y.

[21] Appl. No.: 25,499

[22] Filed: Mar. 3, 1993

Related U.S. Application Data

[63] Continuation of Ser. No. 782,695, Oct. 25, 1991, abandoned.

[51] Int. Cl.$^5$ .................. C07D 487/04; C07D 487/02
[52] U.S. Cl. ................................................ 548/262.4
[58] Field of Search ................................. 548/262.4

[56] References Cited

U.S. PATENT DOCUMENTS

| | | | |
|---|---|---|---|
| 3,705,896 | 12/1972 | Bailey et al. | 548/262.4 |
| 3,725,067 | 4/1973 | Bailey et al. | 96/56.5 |
| 3,758,309 | 9/1973 | Bailey et al. | 96/136 |

FOREIGN PATENT DOCUMENTS

| | | | |
|---|---|---|---|
| 263060 | 12/1988 | Fed. Rep. of Germany | 96/136 |
| 61-144647 | 7/1986 | Japan | 96/136 |
| 61-251684 | 11/1986 | Japan | 96/136 |
| 62-195366 | 8/1987 | Japan | 96/136 |

OTHER PUBLICATIONS

Research Disclosure No. 12443, Aug. 1974, Kenneth Mason Publications, Emsworth, Hampshire, England. Landon.

"Synthesis of 1H-Pyrazolo[3,2-c]-s-Triazoles and Derived Azamethine Dyes", J. C. S. Perkin I, pp. 2047-2052 (1977). Bailey.

*Primary Examiner*—Floyd D. Higel
*Attorney, Agent, or Firm*—Arthur E. Kluegel

[57] ABSTRACT

Process for the formation of 1-H-pyrazolo[3,2-C]-1,2-4-triazoles useful in photographic chemistry as magenta couplers. The products have chlorine or bromine available at the coupling site, and the following formula:

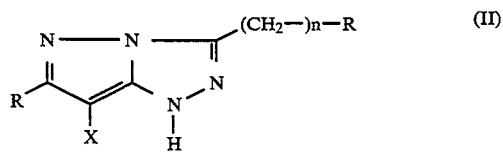

wherein X is chlorine or bromine, n is 0 to 6, and each R is an organic group as defined herein. The compounds are made from a hydrazone by reacting it

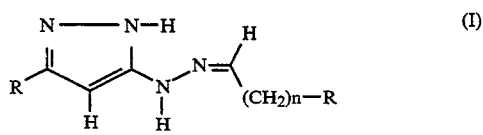

with chlorine or bromine and a base. When the base is a substance such as sodium acetate, the reaction is conducted in one step. When the base is an amine such as a tertiary amine, reaction of (I) is conducted sequentially. Thus, in this second embodiment, (I) is first reacted with chlorine or bromine, and the reaction product thereby produced is treated with the tertiary amine.

7 Claims, No Drawings

PREPARATION OF 1H PYRAZOLO [3,2-C]-S-TRIAZOLE COMPOUNDS

This is a continuation of application Ser. No. 782,695, filed Oct. 25, 1991 now abandoned.

FIELD OF INVENTION

This invention relates to a new process for the preparation of 1H-pyrazolo[3,2-C]-S-triazole rings of general formulas IIa or IIb, known as pyrazolotriazole magenta couplers for color photographic science.

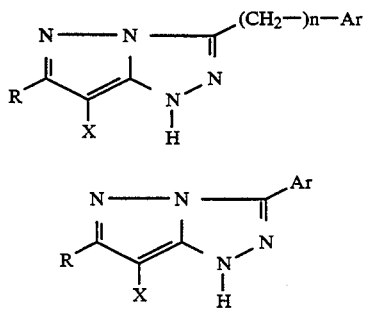

BACKGROUND OF THE INVENTION

Several processes for the synthesis of pyrazolo[3,2-C]-S-triazole magenta couplers are known in the art. However, those processes are lengthy and costly. They employ comparatively toxic intermediates and they involve the use of sulfur materials which pose problems in the photographic process, as well as in ecology; *Research Disclosure* 12443, JP 61/144647, and JP 62/195366. For example, a thermal extrusion of a sulfur atom from a s-triazolo [3,3-b][1,3,4]thiadiazines with ring contraction, is generally used to prepare a pyrazo[3,2-C]-s-triazole magenta coupler. This process is difficult and somewhat hazardous; *Research Disclosure* 12443 and other references mentioned above.

Other processes [J. Bailey et al, *J. Chem, Soc. Perkin*, Trans. 1, 2047 (1977); U.S. Pat. No. 3,725,067 and DD patent 263,060] are also known for the preparation of 1H-pyrazo[3,2C]-S-triazoles by ring closure, followed by subsequent reactions of saponification and decarboxylation of a carboxylic ester functional group.

SUMMARY OF THE INVENTION

The process of this invention comprises reaction of a hydrazone:

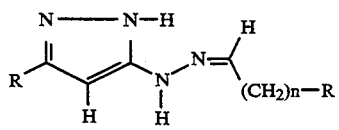

with a halogen and a base, preferably in a suitable solvent. This process can be conducted in two ways: (a) using a sodium salt of a carboxylic acid as the base, or (b) using a tertiary amine as the base. In (a), elemental chlorine or bromine is reacted with (I) in presence of the base (preferably dissolved in an aqueous solution of the corresponding carboxylic acid). In (b), the elemental halogen is reacted with (I) preferably in a solvent such as methylene chloride and the reaction mixture thereby produced is subsequently reacted with the base.

Thus, it can be seen that the invention provides two process expedients, of which both can be practiced using only one reaction vessel.

Compared to the prior art, the invention has many advantages. First, with respect to the method disclosed in *Research Disclosure* 12443, procedures of this invention are simpler and safer to carry out. Second, with respect to other prior art mentioned above, the process of this invention does not require subsequent saponification and decarboxylation steps to prepare the photographic couplers. Third, sulfur intermediates are not involved in the process of this invention; and hence there is lessened risk in contaminating a photographic system with elemental sulfur (which is known to have adverse effect on photographic emulsion speed).

Because the process of this invention is simpler, more readily carried out, does not involve so many steps as the prior art, does not rely on sulfur-containing intermediates, or involve the generation of elemental sulfur contaminant, it is believed to be a significant advance in the art, and well suited for adoption by industry.

DESCRIPTION OF PREFERRED EMBODIMENTS

This invention provides the process for the formation of a pyrazolotriazole coupler, said process comprising reacting a hydrazone compound (I):

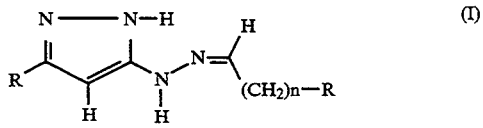

with a halogen and a base, said halogen being chlorine or bromine, and said base being either (i) an alkali metal salt of a lower alkyl carboxylic acid or (ii) a tertiary amine, such that:
  when said base is said alkali metal salt, said halogen is reacted with said compound (I) in the presence of said base, and
  when said base is said tertiary amine, said halogen is reacted with said compound (I) and subsequently the reaction product thereby produced is reacted with said tertiary amine,
whereby said pyrazolotriazole coupler (II):

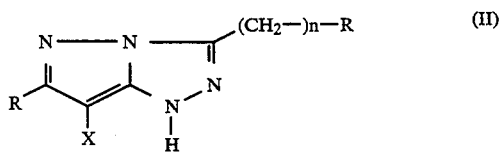

is produced; said process being further characterized by X in the above formula being Cl or Br, n in the above formulas being an integer having a value of 0 to about 6, and each R in said formulas being alike or different and selected from alkyl or aryl groups having up to about 20 carbon atoms.

Thus, the process of this invention involves use of a compound having formula (I). There are two subclasses of these compounds: in one subclass, n is equal to zero, and in the other subclass n is a small whole number of from 1 to about 6. Both subclasses of compounds can be made by reaction of the appropriate hydrazine (or the hydrazine hydrohalide, e.g. hydrochloride)

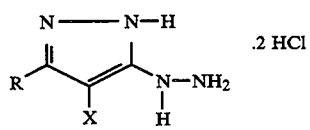

with an aldehyde

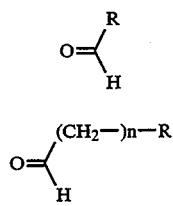

using the skill of the art. When the hydrohalide salt of the hydrazine is used, a base such as a tertiary amine is employed to combine with the hydrogen halide by-product. The preparation of Compound (I) is preferably conducted in a solvent such as methylene chloride or chloroform or acetic acid, or organic chlorinated solvents. Mild temperatures, say −5° to 30° C. are employed, with ambient pressure, and a reaction time of 0.5 to 5.0 hours.

In the process of this invention, Compound (I) is reacted with a halogen, preferably chlorine or bromine. When bromine is used, the reaction is preferably conducted using glacial acetic acid as the solvent. When chlorine is used, methylene chloride is preferably employed as the solvent. It is to be understood that the nature of the solvent is not critical and other solvents which are inert toward the reactants and products, and have the appropriate solvent power for the materials to be dissolved, can be employed. Examples of other suitable solvents are ether, tetrahydrofuran, dioxane.

The reaction can be conducted in the initial presence of base. If it is desired to use this expedient, it is preferred that the base be an alkali metal salt of a carboxylic acid in which the metal is Li, Na, or K, and the acid moiety is a lower alkyl monocarboxylic acid group, e.g. an acid moiety having one to about four carbon atoms and one carboxylic acid group. Thus, preferred salts are R'COOM wherein M is an alkali metal as defined above and R' is hydrogen, or an alkyl group of up to about 3 carbon atoms. Preferred metal salts used as bases in this invention are acetates, and a most preferred base of this type is sodium acetate.

When the reaction is to be conducted in the presence of such a base, one preferably employs a solvent having suitable solvent power for such basic salts. A preferred solvent for this reaction expedient is an acid, R'COOH, wherein R' has the significance assigned above. Thus, a preferred type of solvent is a lower carboxylic acid; most preferably the acid which has the same anion as the base. Thus, acetic acid is a preferred solvent, and is a solvent of choice when a compound of formula (I) is reacted with chlorine or bromine in the initial presence of a base such as sodium acetate.

The process of this invention need not be conducted in the initial presence of a base. As indicated above, a compound of Formula (I) can be reacted with a halogen, and thereafter a base can be added to the reaction mixture to complete the reaction. It is not necessary that the base be an alkali metal salt such as those discussed above. Thus, it can be another type of base such as a tertiary amine. The exact nature of the amine is not critical, one may use pyridine, diethylene triamine, triethylenediamine, or an amine having the formula NR"R",R", wherein each R" is alike or different and is preferably selected from lower alkyl groups, e.g. alkyl groups having one to four carbon atoms. More preferably, all three R" groups are the same. Although trimethylamine can be used, its use is not preferred, since it is a gas under standard conditions. Triethylamine is a preferred tertiary amine.

When an amine is used as a base, it is preferred that the solvent employed not be an acid. Preferably, the solvent is inert to the base, and other ingredients in the reaction system including the desired product. Methylene chloride is a preferred solvent when a base (such as an amine) is added subsequent to contacting the halogen and the compound of formula (I) under reaction conditions.

The processes of this invention are preferably conducted at ambient pressure. They are also usually conducted at a temperature of from about −15° C. to about 150° C.; more preferably from about −10° C. to about 40° C. The reaction time is somewhat dependent on the reaction temperature; higher temperatures favoring faster reaction times. Generally, compounds of Formula (II) are prepared from compounds of formula (I) according to this invention in about 0.5 to about 5.0 hours.

The reactants, halogen and starting material of Formula (I) react in a mole ratio of 1:1. However, it is not necessary to contact the reactants in this mole ratio, and an excess of either reactant can be employed. Generally, a modest excess of halogen is employed in an effort to increase the yield. If desired, chlorine or bromine can be employed in an amount of 1.1 to 3.0 moles per mole of compound of Formula (I). Greater or lesser amounts of halogen can be used. If desired, excess halogen can be removed prior to product work-up, e.g. by removing chlorine using a partial vacuum.

The following examples serve to illustrate the invention but not to limit it.

EXAMPLE 1

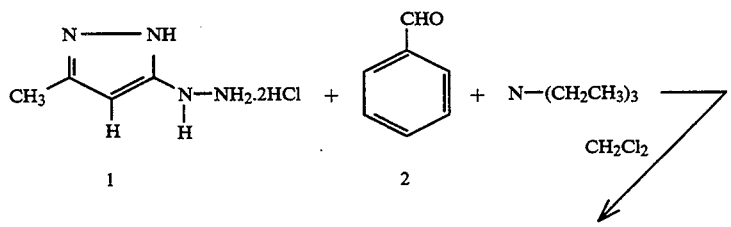

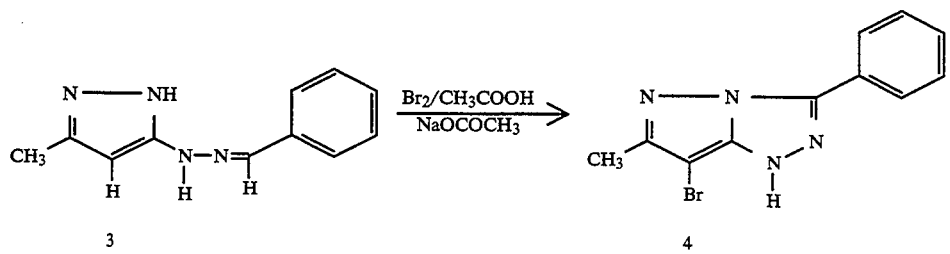

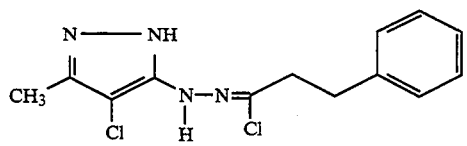

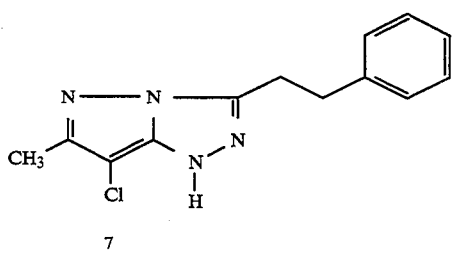

Preparation of hydrazone 3

To a slurry of 18.51 g (0.1 mol) of hydrazine hydrochloride 1 in 120 mL of methylene chloride cooled to −5° C. was added 20.2 g (0.2 mol) of triethyl amine. The slurry was warmed to room temperature and 10.62 g (0.1 mol) of benzaldehyde was added in one portion. A clear orange solution resulted immediately. It was stirred overnight at room temperature. The solvent was removed in vacuo. The thus-obtained solid was stirred in one liter of water for 3 hr. The solid was collected. Washed with water and dried in vacuo. The obtained solid weighed 16.8 g (84%). Spectroscopic data confirmed the desired structure 3.

Preparation of Coupler 4

The hydrazone 3 (2.01 g, 0.01 mol) and sodium acetate (0.984 g; 0.012 mol) were suspended in glacial acetic acid (30mL) and bromine (1.92 g; 0.012 m in 15 mL of glacial acetic acid was added dropwise. After completion of the addition, the reaction mixture was stirred 90 minutes at room temperature and warmed at 100° C. for 25 minutes. Upon cooling, the reaction mixture was poured into 500 mL of cold water with stirring. The resulting precipitate was collected, washed with water and dried in vacuo. The crude material was chromatographed on a short column of silica gel. The purified material gave satisfactory analytical data: Yield of 4 was 1.11 g (40%).

EXAMPLE 2

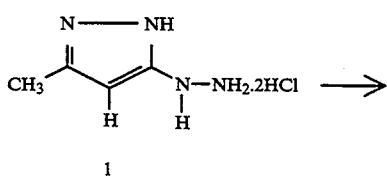

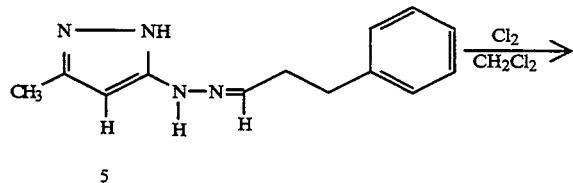

In a 500 mL, 3-necked, round-bottom flask equipped with a magnetic stirrer, a nitrogen inlet and an addition funnel were placed 18.51 g (0.1 mol of 3-methyl-pyrazolone-(5)-hydrazine hydrochlorine 1 and 250 ml of $CH_2Cl_2$. To the resulting yellow slurry, 20.20 g (0.2 mol) of TEA (triethylamine) was added slowly. The slurry dissolved. This was followed by the dropwise addition of 13.42 (0.1 mol) of hydrocinnamaldehyde. After the addition, the reaction was stirred overnight. TLC (thin layer chromatography) showed the reaction to be completed. Water was added. The organic product was extracted with $CH_2Cl_2$. The organic phase was dried and concentrated. A off-white solid resulted. TLC showed one spot material. Spectroscopic data confirmed the assigned structure. The yield of(5) was 20 g (88%).

In a 250 mL, 3-necked, round-bottomed flask equipped with a thermometer, a $N_2$ inlet and a magnetic stirrer were added 2,283 g (0.01 mol) of hydrazone (5) and 40 ml of anhydrous $CH_2Cl_2$. The stirred slurry was cooled to −10° C. (ice and salt bath). Chlorine gas was bubbled into the slurry. The solid dissolved slowly to give a dark red solution. During the reaction with chlorine, the reaction temperature was maintained at −10° C. After the passage of chlorine, the solution was stirred for an additional 20 minutes at −10° C. After that, the reaction was allowed to warm up to room temperature. TLC showed the total disappearance of the starting material. The excess of chlorine and solvent were removed in vacuo.

To the resulting brown semi-solid was added 50 ml of $CH_2Cl_2$ to dissolve the solid. It was cooled to $-10°$ C. Then, 2.21 g (0.022 mol) of TEA in 5 ml of $CH_2Cl_2$ was added dropwise. The reaction temperature was maintained at $-5°$ C. After the addition, the reaction was allowed to warm up slowly to room temperature. It was stirred for an additional 40 min. at room temperature. TLC showed complete reaction. The solvent was removed under vacuum. To the resulting brown solid was added ligroin. The mixture was stirred for 30 min. The solid was collected and dried under suction. It was then stirred in 200 ml of water for 20 min. The solid was collected and dried. TLC showed essentially one spot material. A quick silica gel column chromatography purification of the crude material afforded 1.56 g of desired coupler. Analytical data confirmed the assigned structure (7).

Following the above examples, compounds of Formula (II) can be prepared that have the structures set forth in the following Table. For brevity purposes, Formula (II) is modified somewhat to Formula (IIA), in which $R^2$ is substituted or the symbol $-(CH_2)_n-R$ employed in Formula (II).

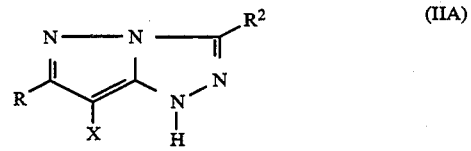
(IIA)

Examples of compounds according to this invention according to Formula IIA are given below, but not limited to these examples.

TABLE

| R | $R^2$ | X |
|---|---|---|
| $(CH_3)_3C-$ | phenyl | Cl |
| $C_2H_5-$ | phenyl | Cl |
| $CH_3-$ | $-CH_2-CH_2-$(4-nitrophenyl) | Cl |
| $C_{16}H_{33}O-$(phenyl)$-$ | $-CH_2-CH_2-$(4-nitrophenyl) | Cl |
| $NO_2-$(phenyl)$-(CH_2)_3-$ | $C_4H_9-$ | Cl |
| $(CH_3)_2CH-$ | $C_4H_9-$ | $-Br$ |
| $C_{12}H_{25}-$ | $n$-$C_6H_{13}-$ | $-Cl$ |
| $CH_3-$ | $-(CH_2)_2-$(4-nitrophenyl) | $-Cl$ |
| $(CH_3)_3C-$ | $-CH_2-CH_2-SO_2-C_{18}H_{37}$ | Cl |

TABLE-continued

| R | R² | X |
|---|----|---|
| (CH₃)₃C— | CH₃CH(H)CH₂—SO₂—C₆H₅ (1-methylethyl phenyl sulfone group) | Cl |
| CH₃— | —CH₂—CH₂—SO₂—C₁₈H₃₇ | Cl |
| (CH₃)₂CH— | 4-(C₁₂H₂₅O)C₆H₄—SO₂—CH₂—CH(CH₃)— | Cl |
| CH₃— | (C₄H₉)(C₂H₅)C(SO₂—C₁₂H₂₅)— | Cl |
| CH₃— | —(CH₂)₃—C₆H₄—NH—C(=O)—CH(C₁₀H₂₁)—O—C₆H₄—SO₂—C₆H₄—OH | Cl |
| CH₃— | 2,4,6-(CH₃)₃C₆H₂—NH—C(=O)—CH(C₁₀H₂₁)—O—C₆H₄—S(O₂)—C₆H₄—O—CH₂—Ph | Cl |

TABLE-continued

| R | R² | X |
|---|-----|---|
| 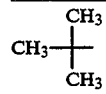 | 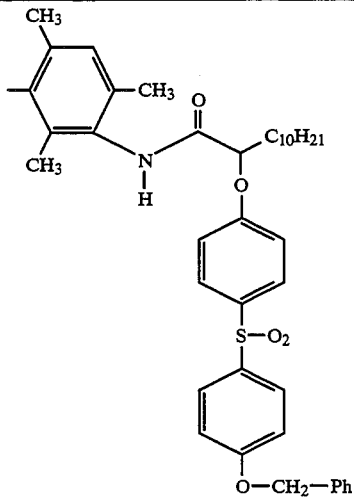 | Cl |
| 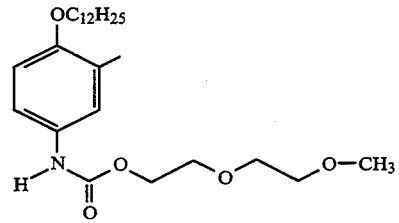 |  | Cl |
| 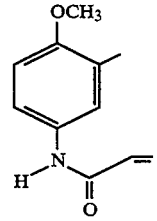 |  | Cl |
| CH₃— | 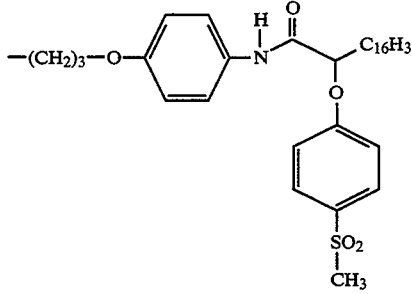 | Cl |
| CH₃— | 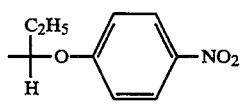 | Cl |

As clear from the above discussion, this invention comprises making compounds in which substituents appear on heterocyclic ring systems.

In addition to the fused rings, the products comprise inert substituents bonded to carbon atoms within the heterocyclic rings, as shown.

For the purpose of this invention, an "inert substituent" or "inert organic group" is defined by having the following characteristics:

(1) It is stable, or substantially stable, under the process conditions employed i.e. it does not decompose to an untoward extent during process(es) employed in this invention.

(2) It is non-reactive, or substantially nonreactive toward the other reagents employed to prepare a compound of this invention: i.e. it does not undergo an extraneous side reaction (to an unacceptable extent) with the other ingredient(s) used in the preparation of a compound of this invention.

(3) It does not prevent, by steric hindrance or other mechanism or effect, the formation of a compound of this invention.

Thus, a wide variety of substituents may appear in the products. In other words, this invention is not critically dependent on the type(s) of groups so long as the groups meet criteria (1), (2) and (3). Typically, the groups are hydrogen or hydrocarbyl groups, i.e. groups which are solely composed of carbon and hydrogen. However, it is not necessary that they solely composed of carbon and hydrogen; thus groups which comprise:

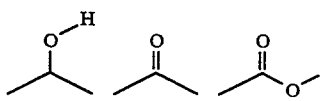

—NH$_2$, NHR$_1$, NR$_1$R$_1$, —SO$_2$—, —S—, —S—S—, and alkoxy, aryloxy, the like, can appear in compounds of this invention, so long as the substituents meet the three criteria enumerated above. Alkyl, cycloalkyl, alkenyl, cycloalkenyl, aryl, alkaryl and aryl groups which meet the criteria can be present in the compounds of this invention. These may be hydrocarbyl, or substituted hydrocarbyl groups, as discussed above. For convenience, R$_1$ and R$_2$ are usually hydrogen or hydrocarbyl groups having up to about 20 carbon atoms; preferably they are hydrogen or alkyl or aryl groups of this type. Lower alkyl radicals (alkyl radicals with up to about 4 carbon atoms) and the phenyl radical are highly preferred.

The R$_3$ radicals are generally selected according to the properties that they confer on the compounds, and/or the role that they play in the selected utility.

On the other hand, the size or nature of the group may be selected because it is produced in a convenient reaction for preparing the pyrazolotriazole starting compound, or the group may be selected to confer some physical or chemical property, such as a desired degree of solubility, or a desired degree of compatibility with other ingredients in a mixture in which the product is used.

Moreover, one or more of the radicals may be selected to contain a radical which contains a reactive site. For example, R$_2$ may be a group having the formula

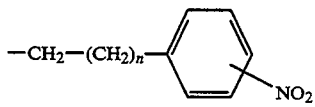

wherein n is a whole number equal to 0 to about 6, and the nitro group is ortho, meta or para to the alkyl side chain. For some uses, it is desirable to subsequently reduce the aryl nitro group to an amino group. Accordingly, it is to be understood that the term "inert" in the phrase "inert substituent" does not mean that the substituent is unreactable in processing conducted after the compound is made.

The invention has been defined with particular reference to preferred embodiments. A skilled practitioner familiar with the above detailed description can make many additions or substitutions without departing from the scope or spirit of the following claims.

We claim:

1. Process for the formation of a pyrazolotriazole coupler, said process comprising reacting a compound:

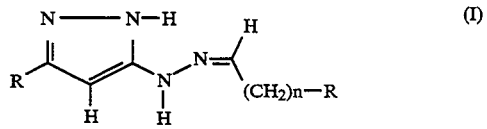

with a halogen and a base, said halogen being chlorine or bromine, and said base being either (i) an alkali metal salt of a lower alkyl carboxylic acid or (ii) a tertiary amine, such that:

when said base is said alkali metal salt, said halogen is reacted with said Compound (I) in the presence of said base, and when said base is said tertiary amine, said halogen is reacted with said Compound (I) and subsequently the reaction product thereby produced is reacted with said tertiary amine, whereby said pyrazolotriazole coupler:

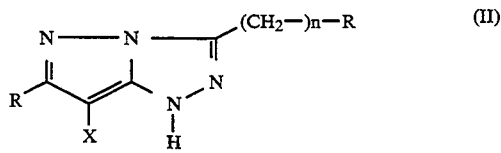

is produced; said process being further characterized by X in the above formula being Cl or Br, n in the above formulas being an integer having a value of 0 to about 6, and each R in said formulas being alike or different and selected from alkyl of aryl groups having up to about 20 carbon atoms.

2. Process of claim 1 wherein n is equal to 0.

3. Process of claim 2 wherein said halogen is bromine, and said base is sodium acetate.

4. Process of claim 3 wherein

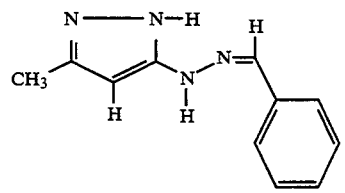

is reacted to form

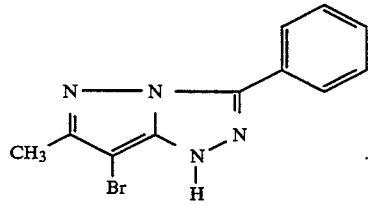

5. Process of claim 1 wherein n is equal to 1 to about 6.

6. Process of claim 5 wherein said base is triethyl amine.

7. Process of claim 6 wherein

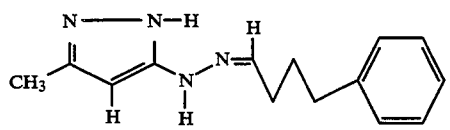
is reacted with chlorine and the halogenated intermediate thereby produced is reacted with triethylamine whereby the coupler
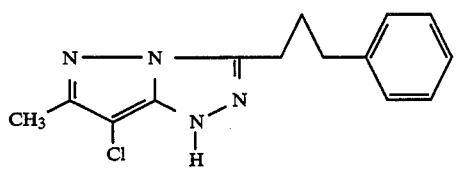
is produced.
* * * * *